United States Patent [19]

Fleming

[11] Patent Number: Plant 7,458

[45] Date of Patent: Feb. 26, 1991

[54] KALANCHOE PLANT NAMED VANGUARD

[75] Inventor: Margaret M. Fleming, Soquel, Calif.

[73] Assignee: The Plant Company, Soquel, Calif.

[21] Appl. No.: 422,089

[22] Filed: Oct. 16, 1989

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Kalanchoe plant named Vanguard particularly characterized by its red-purple flower color; flower diameter of 14 to 16 mm at maturity; flowering response of from 11 weeks in summer to 13 weeks in winter after start of short days; very floriferous habit, with excellent display of many flowers; excellent keeping quality of flowers and foliage; free branching with or without pinching; compact plant habit with intermediate vigor but with short internodes; good responsiveness to B-9 applications to reduce internode length and peduncle elongation; and adaptability to pot sizes from 10 to 15 cm.

2 Drawing Sheets

The present invention relates to a new and distinctive cultivar of Kalanchoe plant, botanically known as *Kalanchoe blossfeldiana* Poelln., and referred to by the cultivar name Vanguard.

Vanguard, identified as 421-005, is a product of a planned breeding program which had the objective of creating new Kalanchoe cultivars for year-round commercial production, with earlier flowering response, good branching yet compact flowering plants, suitability for flowering in pots ranging from 10 to 15 cm, and having good flower and foliage keeping quality.

Vanguard was originated from a cross by the inventor Margaret M. Fleming in a controlled breeding program in Half Moon Bay, Calif., in 1983.

The female parent of Vanguard was the cultivar Sensation, disclosed in U.S. Plant Pat. No. 4,727. The male parent was the cultivar Cinnabar, disclosed in U.S. Plant Pat. No. 5,160.

Vanguard was discovered and selected by the inventor as one flowering plant within the progeny of the stated cross in September, 1984 in a controlled environment in Half Moon Bay, Calif.

The first act of asexual reproduction of Vanguard was accomplished when vegetative cuttings were taken by the inventor from the initial selection in January, 1985 in a controlled environment in Half Moon Bay, Calif.

Horticultural examination of controlled flowerings of successive plantings has shown that the unique combination of characteristics as herein disclosed for Vanguard are firmly fixed and are retained through successive generations of asexual reproduction. Vanguard has not been observed under all possible environmental conditions. The phenotype may vary significantly with variations in environment such as temperature, light intensity and daylength.

The following observations, measurements and comparisons describe plants grown in Soquel, Calif., under greenhouse conditions which approximate those generally used in commercial greenhouse practice.

The following traits have been repeatedly observed and are determined to be basic characteristics of Vanguard, which, in combination, distinguish this Kalanchoe as a new and distinct cultivar:

1. Red-purpose flower color.
2. Flower diameter of 14 to 16 mm at maturity.
3. Flowering response of from 11 weeks in summer to 13 weeks in winter after start of short days.
4. Very floriferous habit, with excellent display of many flowers.
5. Excellent keeping quality of flowers and foliage.
6. Branches freely with or without pinching.
7. Compact plant habit, with intermediate vigor but with short internodes.
8. Responds well to B-9 applications to reduce peduncle elongation.
9. Proper scheduling makes this new cultivar suitable for production in 10 cm to 15 cm pots.

The accompanying photographic drawings show typical inflorescence and leaf characteristics of Vanguard, with colors being as nearly true as possible with illustrations of this type.

Sheet 1 is a color photograph of Vanguard grown as a non-pinched flowering Kalanchoe in a 10 cm pot.

Sheet 2 is a black and white photograph showing the leaves of Vanguard at three stages of development (mature, intermediate and immature).

Of the commercial cultivars known to the inventor, the most similar in comparison to Vanguard is the cultivar Singapore, disclosed in U.S. Plant Pat. No. 5,361. Similar traits are flower color, flowering response, responsiveness to B-9, and adaptability to various pot sizes. Vanguard's habit is more compact with shorter internodes and more free branching than Singapore. The better branching results in a large head of flowers than Singapore. In addition, Vanguard exhibits a better keeping quality of flowers and foliage than Singapore.

In comparison to the female parent Sensation, Vanguard is taller and has longer internodes than Sensation, and presents a larger display because of its open branching habit. The red-purple flower color of Vanguard is much deeper than the pink color of Sensation, although both cultivars share a certain brightness or luminescence. The foliage of Vanguard is entirely different than the foliage of Sensation, or the foliage of any other variety known to the inventor. The foliage of Vanguard is more fleshy than that of Sensation, deeper green in color, and under conditions of high light intensity the leaf margins tend to become red. These characteristics have not been observed on plants of Sensation grown under the same conditions.

When Vanguard is compared to the male parent Cinnabar, fundamental differences are readily apparent. Vanguard differs from Cinnabar in flower color, petal shape, flowering response, form and color of foliage, and its long keeping characteristic. Vanguard is as long keeping as any of the new cultivars.

In the following description color references are made to The Royal Horticultural Society Colour Chart. The color values were determined on plant material grown as a non-pinched pot plant in a 10 cm pot in Soquel, Calif., on Aug. 9, 1988.

Classification:

*Botanical.*—*Kalanchoe blossfeldiana* Poelln. cv. Vanguard.

*Commercial.*—Flowering pot Kalanchoe.

Parentage:

*Female parent.*—Sensation (U.S. Plant Pat. No. 4,727).

*Male parent.*—Cinnabar (U.S. Plant Pat. No. 5,160).

Propagation:

(A) *Type cutting.*—Short tip cutting, with stems up to 2 cm.

(B) *Time to root.*—10 days at 21° C. in summer, 14 days at 21° C. in winter.

(C) *Rooting habit.*—Many very fine roots, fibrous.

Plant Description:

(A) *Form.*—Short internodes, upright growth. Growing and scheduling practices can produce a small plant in a 10 cm pot up to a larger plant in a 15 cm pot.

(B) *Habit of growth.*—Rate of growth moderate for this type of plant. Generally, shoots are formed at every node; internode length of natural vegetative plant, 15–35 mm.

(C) *Height.*—The overall plant height of Vanguard at the time of flowering ranges from approximately 15–25 cm. above a 10 cm. pot. This is based on a schedule of 4–6 weeks of long day treatment prior to the start of short day treatment, no pinch, and 3–4 applications of 3500 ppm B-9 SP.

*Foliage description.*—Leaves simple, opposite, slightly lobed. Frequently leaves are asymmetrical, with a tendency to twist or bend. 1. Size: Average full grown leaf in a 10 cm flowering pot is 125 mm long × 67 mm wide. 2. Shape: Ovate to elliptic, apex obtuse, base attenuate. 3. Texture: Glabrous, coriaceous, succulent. 4. Margin: Sinuate to crenate. 5. Color: Mature foliage: Upper surface 147A. Under surface 147B. Under certain conditions tips and margins of mature foliage on both upper and under surface are slightly streaked with 183A to 183C. 6. Durability: Excellent; no degradation observed even on the lower foliage of plants retained for months beyond normal life expectancy.

Flowering Description:

(A) *Flowering habit.*—Inflorescence of each shoot is formed by dichotomous branching, starting with opening of terminal flower of main axis, followed by terminal flowers of the side branches, continuing with subsequent development of branches in the inflorescence. Opening of new buds (12–17 mm. in length) will continue for two months or more. Individual flowers last two weeks or more after opening.

(B) *Flowering response.*—Flowering time under controlled daylength after start of short days is 11 weeks in summer to 13 weeks in winter.

(C) *Flowers borne.*—Compound dichasial cymes; peduncle length depends upon schedule, environmental conditions, B-9 applications, location upon the plant, and inherited vigor. The peduncle length range of Vanguard is 5–12 cm. and the diameter 4–8 mm., with the longest peduncle supporting the central inflorescence. Pedicel length varies from 5–7 mm., and diameter is approximately 1 mm., depending upon the same factors.

(D) Quantity of flowers.—Very floriferous; there are up to 100 florets per major inflorescence, and up to 500 florets per plant in a 10 cm. pot using commercial culture techniques; up to 4–6 side laterals in a 10 cm. pot.

(E) *Petals.*—1. Shape: Slightly pointed to almost round. 2. Color: Upper surface: Closest to 57A. Under surface: Margins 57D to center 56A. 3. Number of petals: 4, united in corolla. 4. Flower diameter: 14 to 16 mm at maturity.

(F) *Reproductive organs.*—1. Stamens: 8 in number. a. Anther shape: Flat, elliptical, color yellow. b. Filament color: Light green. c. Pollen color: Yellow. 2. Pistils a. Stigma shape: Flat, crystalline, color greenish white. b. Style color: Light green. c. Ovaries: 4-celled, color light green.

(G) *Keeping quality.*—Excellent, flowers last two weeks or more, with the plant being in flower two months or more.

Disease Resistance: No flower or foliage diseases or problems have been noted to date. Vanguard is resistant or immune to Botrytis, and there is no fading or color breaking. It is also resistant or immune to the foliar disease Powdery Mildew, and has not exhibited any problems with regard to chlorosis, necrotic spot, tip die-back, root rot, or stem rot. To date, Vanguard has been essentially trouble-free in commercial production.

Fragrance: None perceived in flowers or foliage.

I claim:

1. A new and distinct plant of Kalanchoe named Vanguard, as described and illustrated.

* * * * *

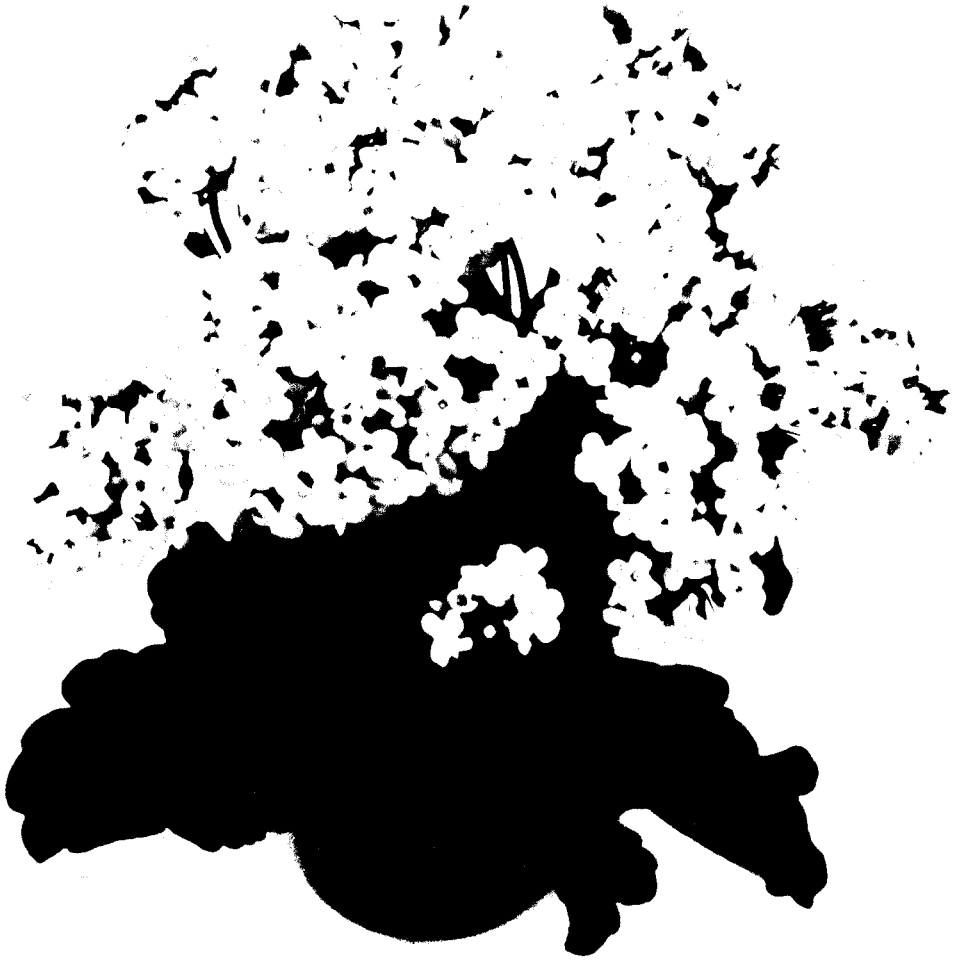

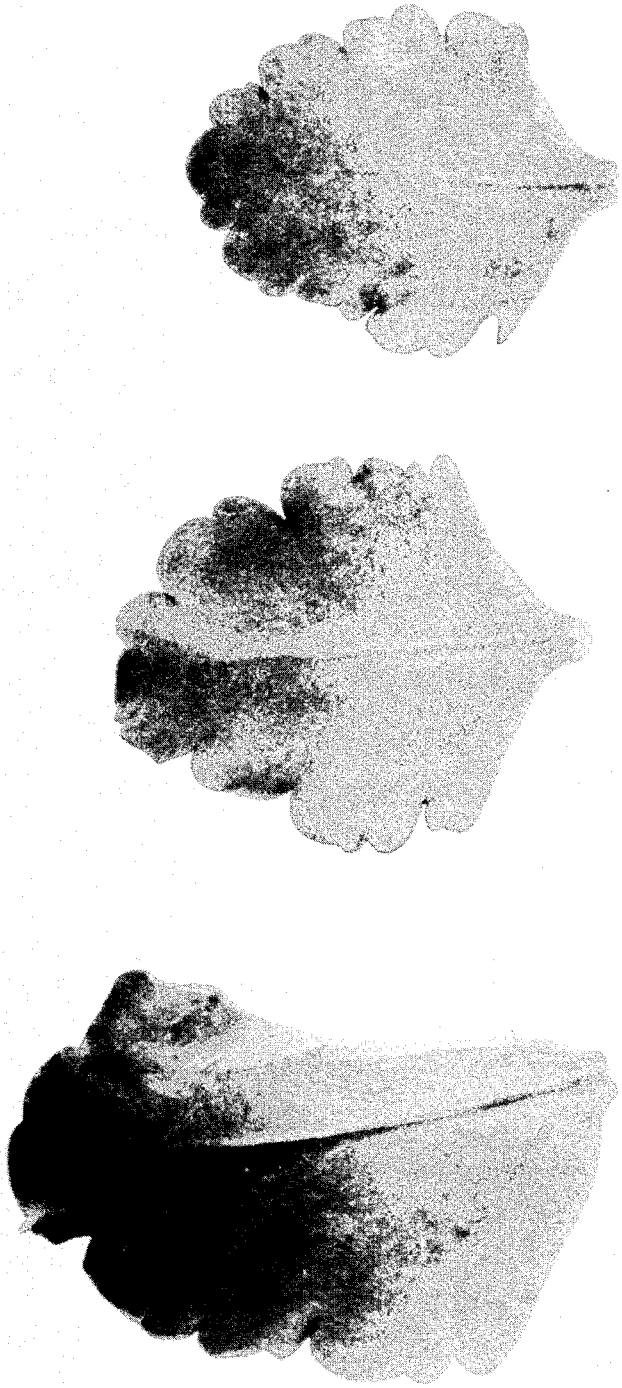
VANGUARD